(12) United States Patent
Iwaki et al.

(10) Patent No.: US 6,858,392 B2
(45) Date of Patent: Feb. 22, 2005

(54) BLOCKING OF DEVICE FOR DETECTING BIOCHEMICALLY ACTIVE MOLECULES

(75) Inventors: Yoshihide Iwaki, Saitama (JP); Hiroshi Shinoki, Saitama (JP); Osamu Seshimoto, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 125 days.

(21) Appl. No.: 10/021,840

(22) Filed: Dec. 13, 2001

(65) Prior Publication Data

US 2002/0110903 A1 Aug. 15, 2002

(30) Foreign Application Priority Data

Dec. 13, 2000 (JP) ........................................ 2000-379332

(51) Int. Cl.$^7$ .......................... C12Q 1/68; G01N 33/53; C07H 21/00; C12P 19/34
(52) U.S. Cl. .......................... 435/6; 435/7.1; 435/91.1; 435/91.2; 435/287.2; 536/22.1; 536/23.1; 536/24.3
(58) Field of Search ............................ 435/6, 7.1, 91.1, 435/91.2, 287.2; 536/22.1, 23.1, 24.3–24.33

(56) References Cited

U.S. PATENT DOCUMENTS 4,822,731 A    4/1989   Watson et al.

FOREIGN PATENT DOCUMENTS

| EP | 0 221 308 | 5/1987 |
| EP | 0 838 221 A | 4/1998 |
| WO | WO 92/03579 | 3/1992 |
| WO | WO 92/07093 A | 4/1992 |
| WO | WO 97/14815 A | 4/1997 |

OTHER PUBLICATIONS

Van Ness J. et al., "A Versatile Solid Support System for Oligodeoxynucleotide Probe–Based Hybridization Assays," Nucleic Acids Research, Oxford Univ. Press, vol. 19, No. 12.

*Primary Examiner*—Kenneth R. Horlick
*Assistant Examiner*—Joyce Tung
(74) *Attorney, Agent, or Firm*—Reed Smith LLP

(57) ABSTRACT

A process for blocking a device for detection of biochemically active molecules is performed by the steps of:

bringing in the presence of an aqueous medium a detection device having probe molecules, ionic reactive groups, and non-ionic reactive groups on its surface, into contact with compounds which react with the non-ionic reactive groups to produce covalent bondings and compounds which form electrostatic bondings with the ionic reactive groups, simultaneously or separately; and washing the surface of the detection device with an aqueous solvent or a water-miscible solvent.

16 Claims, 5 Drawing Sheets

(I)

(IIIa)

Blocker (IVa)

A

B

C

D

E

F

G

H

I

BLOCKING OF DEVICE FOR DETECTING BIOCHEMICALLY ACTIVE MOLECULES

FIELD OF THE INVENTION

This invention relates to a process for blocking a device of detecting biochemically active molecules such as a DNA detection device.

BACKGROUND OF THE INVENTION

Gene structures of various living bodies as well as the functions of genes in genome scale have been widely studied. Accordingly, new technology for analyzing the gene functions has been rapidly developed.

A DNA micro-array (i.e., DNA chip) which is composed of a solid carrier (i.e., substrate) and a great number of spots of probe molecules such as DNA fragments or oligonucleotide molecules which are aligned and fixed on the solid carrier in separated areas is generally employed not only for base sequencing of a nucleic acid but also analyzing expression, mutation and polymorphism of gene. The analytical data of genetic information are favorably employable also for the study of pharmacologically active substances and further for diagnosis and prevention of diseases.

In the procedure for detection of a nucleic acid such as DNA fragment using the DNA micro-array, a nucleic acid sample (i.e., target nucleic acid) which is equipped with a radioisotope (RI) label or a fluorescent label is brought into contact with the probe molecules in the spots of the micro-array. If the target nucleic acid is complementary to the probe molecules in a certain base sequence, the target nucleic acid is combined with the probe molecules by hybridization. Thus hybridized target nucleic acid is detected by sensing its radioisotope label or fluorescent label. The results of the detection are then imagewise analyzed. The analytical procedure using the DNA micro-array can give a great number of data on the target nucleic acid simultaneously employing an extremely small amount of the target nucleic acid.

A DNA micro-array is prepared generally by synthesizing probe molecules (such as oligonucleotides) on a solid carrier (which is called "on-chip method") or by fixing onto a solid carrier a number of previously prepared DNA fragments or oligonucleotides.

The former on-chip method is performed by synthesizing a number of oligonucleotides by combinatrial synthesis in each of extremely small areas predetermined on the solid carrier. In the synthetic procedure, photo-lithography and solid synthesis technology are utilized and a protective group is selectively removed by irradiation of light.

In the latter method, the previously prepared probe molecules such as DNA fragments or oligonucleotides are spotted on a solid carrier in each of the predetermined small areas and fixed onto the carrier by covalent bonding or ionic bonding (i.e., electrostatic bonding). The bonding is generally produced in the manner described below.

(1) In the case that the probe molecule is a DNA fragment such as cDNA fragment (i.e., complementary DNA fragment which is synthesized using mRNA as template) or a PCR product (i.e., DNA fragment produced from cDNA by multiplication procedure), an aqueous solution of the DNA fragments is spotted on a solid carrier having a coat of a polycation compound (such as poly-lysine or polyethyleneimine) by means of a spotting device of a micro-array preparing apparatus so that the DNA fragments can be electrostatically fixed onto the solid carrier utilizing electric charge of each DNA fragment.

(2) In the case that the probe molecule is a synthesized oligonucleotide, a reactive group is previously incorporated into the oligonucleotide. The oligonucleotide having the reactive group is then brought into contact with a solid carrier which has a reactive group on its surface in an aqueous medium using a spotting means so that the desired covalent bonding is produced between the reactive group of the oligonucleotide and the reactive group of the solid carrier. Examples of the reactive groups to be incorporated into the oligonucleotide include amino, aldehyde, mercapto (—SH), and biotin. On the surface of the solid carrier, a silane coupling agent having amino, aldehyde, epoxy, or the like is coated to incorporate the reactive group onto the surface. The fixation of oligonucleotide by covalent bonding is advantageous because it can produce bonding which is highly stable, as compared with the electrostatic bonding.

(3) In the case that the probe molecule is PNA (i.e., Peptide Nucleic Acid), a reactive group is previously incorporated into the probe PNA in the same manner as in the case (2) as above using the oligonucleotide.

It is preferred that the detection devices (e.g., DNA micro-array) prepared in the above-described preparing methods have probe molecules only on the solid carrier, because it electrostatic groups or reactive groups remain on the solid carrier with no cap groups, target molecules having a sensible label such as a fluorescent label may combine not only with the probe molecules but also with the electrostatic groups or reactive groups. The target molecules having been combined with the electrostatic groups and/or reactive groups produce noises in the analytical procedures.

It is already known to employ a blocking agent for obviating production of unfavorable combination between the target molecules and the electrostatic groups and/or reactive groups. The blocking agent can be employed by bringing the blocking agent into contact with a detection device having reactive groups and/or electrostatic groups on its surface. A representative blocking agent available on market is Denhaldt's solution. For blocking a detection device on which reactive groups remain on its surface, an aqueous monoethanol amine solution is known.

WO 97/14815 describes blocking a detection device using succinic anhydride or its analogue compound.

SUMMARY OF THE INVENTION

It is an object of the present invention to provide a process for preparing a detection device (e.g., micro-array for analysis of DNA or DNA fragment), which gives high detection accuracy and low detection error.

Particularly, it is an object of the invention to provide a process for blocking a device of detecting biochemically active molecules such as DNA fragments and proteins.

The present invention resides in a process for blocking a device for detection of biochemically active molecules which comprises the steps of:

bringing in the presence of an aqueous medium a detection device having probe molecules, ionic reactive groups, and non-ionic reactive groups on a surface thereof, into contact with compounds which react with the non-ionic reactive groups to produce covalent bondings and compounds which form electrostatic bondings in conduction with the ionic reactive groups, simultaneously or separately; and washing the surface of the detection device with an aqueous solvent or a water-miscible solvent.

The invention also resides in a device for detection of biochemically active molecules which is blocked by the above-described process.

In the above-described process of the invention, preferred are as follows.

(1) The compounds which react with the non-ionic reactive groups to produce covalent bondings and the compounds which form electrostatic bondings in conduction with the ionic reactive groups are present in one aqueous solution.

(2) The aqueous medium contains a surface active agent, particularly an anionic surface active agent (e.g., sodium dodecyl sulfate).

(3) The ionic reactive groups are amino groups or mercapto groups.

(4) The ionic reactive groups are amino groups and the compounds which form electrostatic bondings in conduction with the ionic reactive groups are dextran sulfates.

(5) The non-ionic reactive groups are ethylenic unsaturated groups.

(6) The ethylenic unsaturated groups are vinyl sulfonyl groups or their precursors having the following formula:

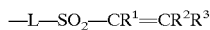

—L—SO$_2$—CR$^1$=CR$^2$R$^3$ wherein each of R$^1$, R$^2$ and R$^3$ independently is a hydrogen atom, an alkyl group having 1 to 6 carbon atoms, an aryl group having 6 to 20 carbon atoms, or an aralkyl group having 7 to 26 carbon atoms in which its alkyl group has 1 to 6 carbon atoms, and L is a linking group (7) The non-ionic reactive groups are ethylenic unsaturated groups and the compounds which react with the non-ionic reactive groups to produce covalent bondings are amino group-containing compounds.

(8) The amino group-containing compounds are glycines.

(9) The probe molecules are nucleotide derivatives selected from the group consisting of oligonucleotides, polynucleotides, and peptide nucleic acids.

(10) The probe molecules, ionic reactive groups, and non-ionic reactive groups are fixed on the detection device by covalent bonding.

The invention further resides in an aqueous solution containing an amino group-containing compound showing a positive charge, an acidic compound showing a negative charge, and an anionic surface active agent.

In the above-mentioned aqueous solution, it is preferred that the amino group-containing compound is glycine, and the acidic compound is dextran sulfate.

The invention furthermore resides in a process for blocking a device for detection of biochemically active molecules which comprises the steps of:

bringing in the presence of an aqueous medium a detection device having probe molecules and ionic reactive groups on a surface thereof, into contact with compounds which form electrostatic bondings in conduction with the ionic reactive groups; and washing the surface of the detection device with an aqueous solvent or a water-miscible solvent.

In the above-described process of the invention, preferred are as follows.

(1) The aqueous medium contains a surface active agent, particularly an anionic surface active agent.

(2) The ionic reactive groups are amino groups or mercapto groups.

(3) The ionic reactive groups are amino groups and the compounds which form electrostatic bondings in conduction with the ionic reactive groups are dextran sulfates.

(4) The probe molecules are nucleotide derivatives selected from the group consisting of oligonucleotides, polynucleotides, and peptide nucleic acids.

(5) The probe molecules are fixed on the detection device by electrostatic bonding and ionic reactive groups are fixed on the detection device by covalent bonding.

The invention furthermore resides in a device for detection of biochemically active molecules which is blocked by the above-mentioned process.

The invention furthermore resides in a device for detection of biochemically active molecules which is blocked by the above-mentioned process.

DETAILED DESCRIPTION OF THE INVENTION

Figure 1:
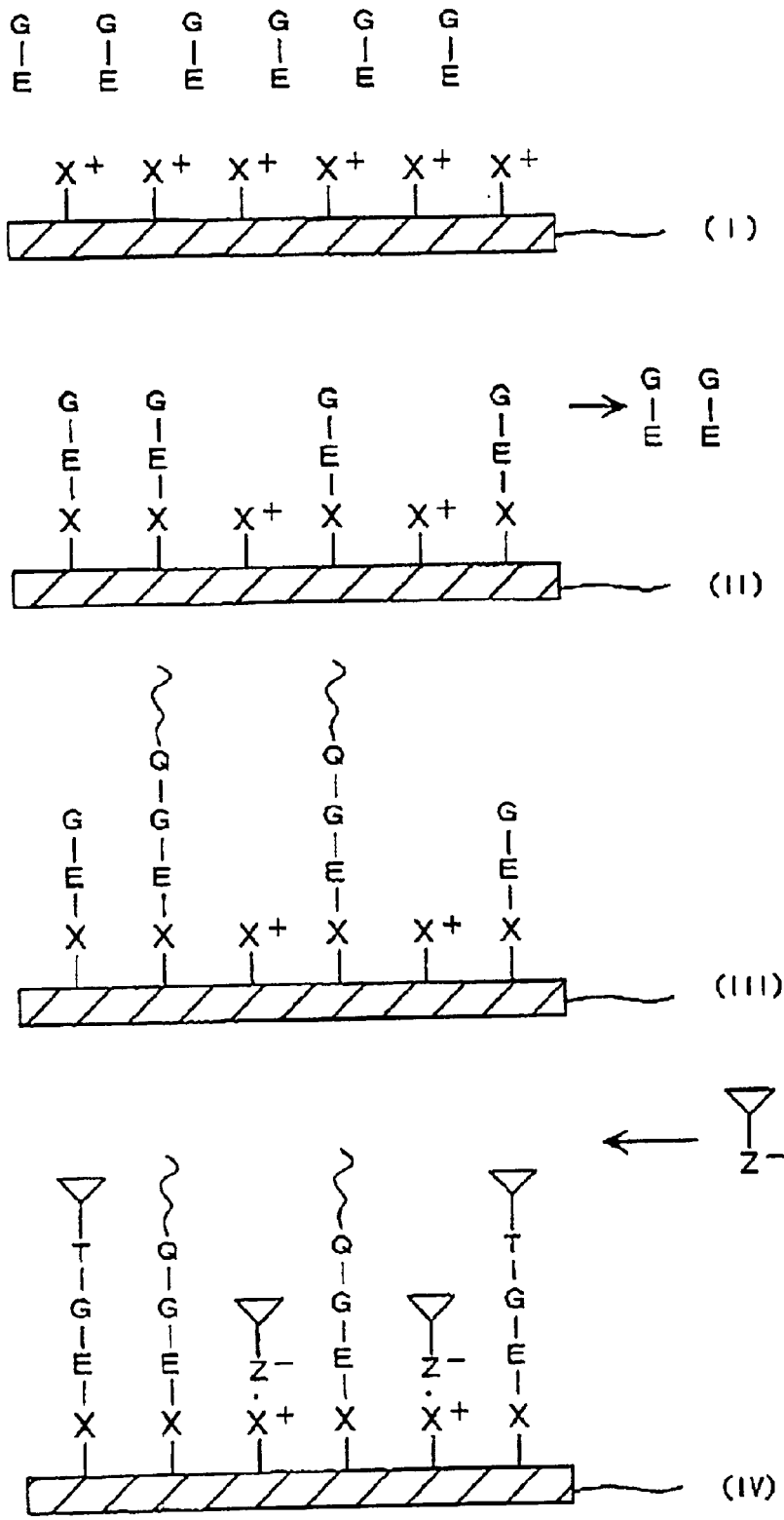
FIG. 1 schematically illustrates a blocking process of the invention which is applicable to a detection device on which probe molecules are fixed covalently.

A typical blocking process of the invention which is applicable to a detection device on which probe molecules are fixed covalently is illustrated in FIG. 1.

The solid carrier (I) having ionic reactive groups X$^+$ (e.g., amino groups —NH$_2$ or mercapto groups —SH) on its surface is brought into contact with a reactive compound having two reactive groups E, G (e.g., divinylsulfonic compound) in which E reacts with the ionic reactive group X$^+$ to produce a covalent bonding. G can be equal to or different from E.

The solid carrier (II) now has the reactive compounds on some of the ionic reactive groups X$^+$. However, some reactive groups X$^+$ remain unreacted on the solid carrier.

The solid carrier (II) is then brought into contact with probe molecules having a reactive group Q so that the solid carrier (III) having the probe molecules covalently fixed on the carrier. However, some reactive groups G remain unreacted on the solid carrier.

The solid carrier (III) is then subjected to the blocking process of the invention which employs a combination of blocking agents (i.e., blockers) in the presence of an aqueous medium. The blockers comprises a blocker having an ionic group Z$^-$ which forms electrostatic bonding with the ionic reactive group X$^+$ and a blocker having a reactive group T which reacts with the reactive group G remaining on the solid carrier. In the aqueous medium which preferably contains one or two blockers, a surface active agent such as an anionic surface active agent is preferably incorporated.

Finally, the solid carrier (IV) having been blocked by the combination of blockers is washed with an aqueous solvent (e.g., water, preferably a boiling water) or a water-immiscible solvent (e.g., a lower alcohol) and then dried.

The blocking agent having the ionic group Z$^-$ preferably is dextran sulfate, mucopolysaccharide having a sulfonyl group, taurine having a sulfonyl group, polypeptide having a carboxyl group, or polysaccharide having a carboxyl group. An aqueous solution containing the blocking agent preferably further contains a buffer compound such as glycine.

The blocking agent having the reactive group T preferably is a compound having an amino group, a mercapto group, or a hydroxyl group. Preferred are compounds having active hydrogen atom such as glycine.

Figure 2:
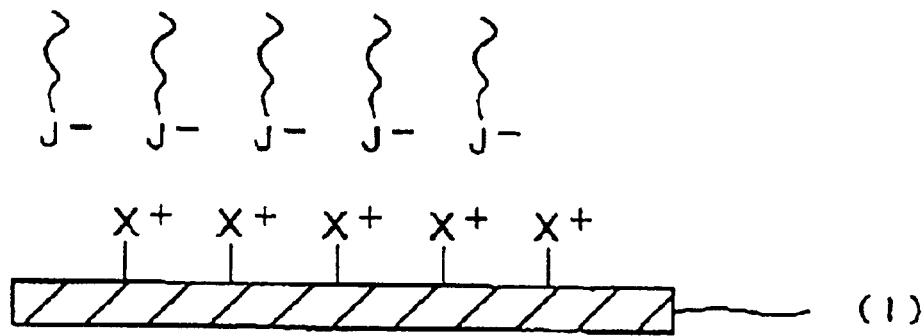
FIG. 2 schematically illustrates a blocking process of the invention which is applicable to a detection device on which probe molecules are fixed by electrostatic bonding.
Figure 2:
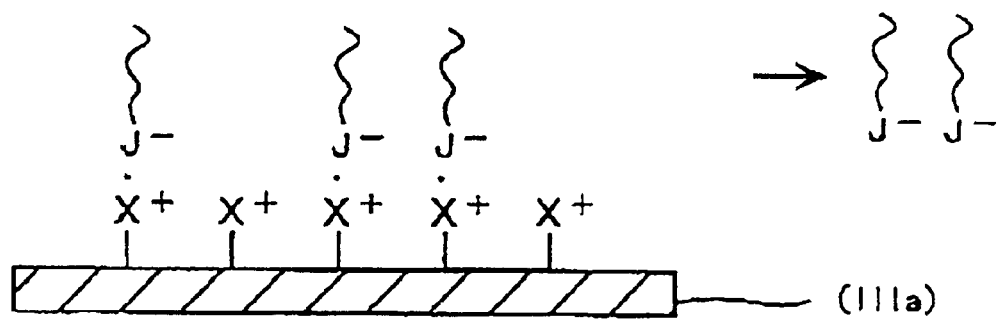
Figure 2:
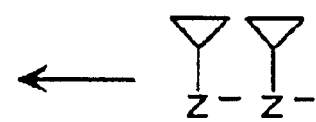
Figure 2:
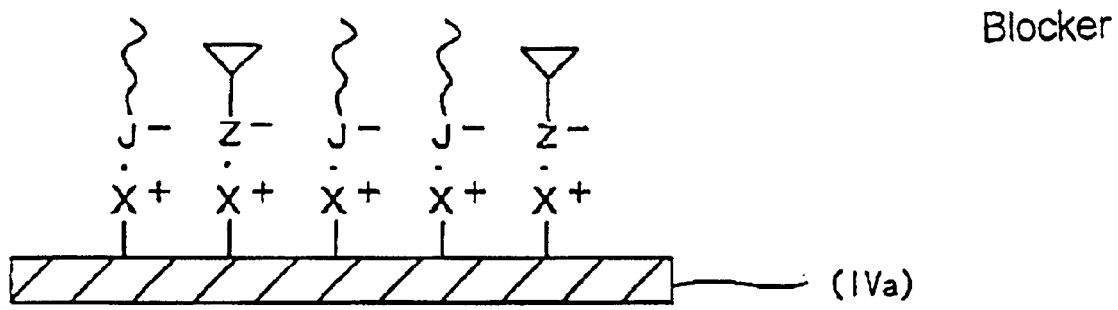

A typical blocking process of the invention which is applicable to a detection device on which probe molecules are fixed by electrostatic bonding is shown in FIG. 2.

The solid carrier (I) having ionic reactive groups $X^+$ (e.g., amino groups $-NH_2$ or mercapto groups $-SH$) on its surface is brought into contact with probe molecules having an ionic group $J^-$ so that the solid carrier (IIIa) having the probe molecules electrostatically fixed on the carrier. However, some ionic reactive groups $X^+$ remain unreacted on the solid carrier.

The solid carrier (IIIa) is then subjected to the blocking process of the invention which employs a blocking agent (i.e., blocker) in the presence of an aqueous medium. The blocker has an ionic group $Z^-$ which forms electrostatic bonding with the ionic reactive group $X^+$ remaining on the solid carrier. In the aqueous medium which preferably contains the blocker, a surface active agent such as an anionic surface active agent is preferably incorporated.

Finally, the solid carrier (IVa) having been blocked by the blocker is washed with an aqueous solvent (e.g., water, preferably a boiling water) or a water-immiscible solvent (e.g., a lower alcohol) and then dried.

The solid carrier can be any of known solid carriers or their equivalent materials, for instance, a glass plate, a ceramic plate, a resin plate, a metal plate, a glass plate covered with polymer coat, a glass plate covered with metal coat, and a resin plate covered with metal coat. The solid carrier may have a porous structure.

In order to fix probe molecules onto the solid carrier by covalent bonding, the solid carrier should have a plurality of ionic reactive groups on its surface. The ionic reactive groups are provided to the solid carrier, for instance, by coating its surface with a poly-cationic compound (e.g., poly-L-lysine, polyethyleneimine, or polyalkylimine). The poly-L-lysine coat is preferred. Otherwise, the surface of the solid carrier can be treated with a silane-coupling agent containing an ionic reactive group (e.g., amino or mercapto), so that the ionic reactive group is provided to the surface of the solid carrier.

The ionic reactive group preferably is an amino group. When the silane-coupling agent is employed, the silane-coupling agent is fixed onto the surface of the solid carrier via covalent bonding. When the amine group-containing polymer is employed, the polymer is fixed onto the surface of the solid carrier by electrostatic bonding. The covalent-bonding is preferred from the viewpoint of stable and reliable fixation.

Examples of the silane-coupling agents include γ-aminopropyltriethoxysilane, N-β (aminoethyl)-γ-aminopropyltrimethoxysilane, and N-β (aminoethyl)-γ-aminopropylmethyldimethoxysilane. Most preferred is γ-aminopropyltriethoxysilane.

A combination of processing a solid carrier with a silane-coupling agent in combination with coating with a poly-cation is also employable.

Examples of commercially available solid carrier having the pre-treated surface include PLL (polylysine-coated plate, available from Sigma Corp.), CMT-GAPS (aminosilane-coated plate, available from Corning Corp.), MAS (aminosilane-coated plate, available from Matsunami Glass Co., Ltd.), Silanate (polysilane-coated plate, available from Gliner Corp.), Sinelite (polysilane-coated plate, available from Telechem Corp.), DNA-Ready Type I or II Slide (aminosilane-coated plate, available from Clonetech Corp.), Sililate (silane aldehyde-coated plate, available from Gliner Corp.), Sililate (silanealdehyde-coated plate, available from Telechem Corp.), and 3D-Link (active carboxylic acid-treated plate, Thermotex Corp.).

The probe molecules such as DNA fragments or synthetic oligonucleotides are then fixed on the surface of the solid carrier. The procedure for fixing the probe molecules onto the solid carrier is performed by bringing an aqueous solution of the probe molecules into contact with the surface of the solid carrier. For fixation of the probe molecules onto the solid carrier by covalent bonding, the probe molecules preferably have a reactive group which is combined with the reactive groups of the solid carrier using a linking chain which can be produced, for instance, using a compound having ethylenic unsaturated groups.

Preferably, the ethylenic unsaturated groups are vinylsulfonyl groups or their precursors having the following formula:

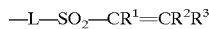

wherein each of $R^1$, $R^2$ and $R^3$ independently is a hydrogen atom, an alkyl group having 1 to 6 carbon atoms, an aryl group having 6 to 20 carbon atoms, or an aralkyl group having 7 to 26 carbon atoms in which its alkyl group has 1 to 6 carbon atoms, and L is a linking group.

The compounds having the vinylsulfonyl groups preferably have the following formula:

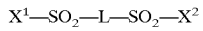

in which each of $X^1$ and $X^2$ is a vinyl group and L is a linking group.

Representative vinylsulfonyl-containing compounds are 1,2-bis(vinylsulfonylacetamide)ethane or 1,2-bis(vinylsulfonylacetamide) propane.

Otherwise, the linking chain can be made of an alkylene group such as hexylene group or an N-alkylamino-alkylene group such as N-methylamino-hexylene group.

The probe molecule may be a peptide nucleic acid (i.e., PNA) which can be produced by changing the phosphodiester bonding of DNA with a peptide bonding.

In the process of the invention, the probe molecules can be fixed onto the solid carrier by electrostatic bonding. The fixation of probe molecules onto a solid carrier per se is already known. For instance, a glass sheet is treated by an aminosilane coupling agent or coated with a polycation compound (e.g., poly-lysine or polyethyleneimine) so that a cationic group is fixed onto the glass sheet. Thus treated glass sheet is brought into contact with a DNA fragment having an anionic group such as a phosphoric acid group (or phosphate group) or a synthesized oligonucleotide or PNA into which an appropriate anionic group is introduced, so that an electrostatic bonding can be formed between the solid carrier and the probe molecules.

For the fixation of probe molecules onto the solid carrier, the probe molecules and optionally water-soluble thickening agent are dissolved or dispersed in an aqueous medium such as distilled water or SSC (i.e., Standard Salt-Citrate buffer, or brine and citrate buffer) to prepare an aqueous probe molecule solution for spotting. The aqueous probe molecule solution generally has a viscosity in the range of 1 to 100 mPa·s. When the spotting is done by means of a spotter of quill-pin type, the aqueous solution preferably has a viscosity of 2 to 50 mPa·s, more preferably a viscosity of 2 to 20 mPa·s. If the thickening agent is a water-soluble polymer, the polymer is preferably dissolved in an aqueous medium in an amount of 0.1 to 5 wt. %, more preferably in an amount of 0.3 to 3 wt. %. If the thickening agent is a polyhydric alcohol or saccharide, it is preferably dissolved in an aqueous medium in an amount of 5 to 50 wt. %, more preferably in an amount of 10 to 40 wt. %.

Generally, the aqueous solution is once placed on a plastic plate having 96 or 384 wells, and then spotted onto a solid carrier using a spotting means. The spotting means of pin type in which the aqueous solution can be held is generally employed. The pin holding the solution was then brought into contact with the surface of the solid carrier to transfer the solution onto the solid carrier. The pin may be a solid pin which has no groove on its tip or a quill pin which has a groove on its tip. The quill pin is preferably employed. Other known spotting system such as an ink jet system or a capillary system are also utilizable.

The aqueous solution is spotted onto the solid carrier under the condition that each drop of the solution generally has a volume of 100 pL to 1 $\mu$L, preferably 1 to 100 nL. The probe molecules are preferably spotted onto the solid carrier in an amount of $10^2$ to $10^5$/cm$^2$. In terms of mol. of the probe molecule, 1 to $10^{-15}$ moles are placed in each spot. In terms of weight, several ng or less of probe molecules are placed in each spot. The spotting of the aqueous solution is done onto the solid carrier to form a great number of dots (i.e., spots) having almost the same shape and size. It is important to form these dots to have almost the same shape and size, if the hybridization is to be quantitatively analyzed. Several dots are formed separately from each other with a distance of 1.5 mm or less, preferably 100 to 300 $\mu$m. One dot preferably has a diameter of 50 to 300 $\mu$m.

The known DNA micro-array has on its surface a great number of dots or spots formed of probe molecules. The probe molecules present in one spot are generally equal to each other. However, the probe molecules present in different spots may be the same or different.

After the aqueous solution is spotted on the solid carrier, the spotted solution is incubated, namely, for keeping the spotted solution for a certain period of time at room temperature or under warming (at 25–50° C. and 70% RH or higher), so as to firmly fix the spotted probe molecules onto the carrier surface. In the course of incubation, UV irradiation or surface treatment using sodium borohydride or a Shiff reagent may be applied to the spotted solution. The UV irradiation under heating is preferably adopted. It is assumed that these treatments are effective to strengthen the desired covalent bonding between the surface of the solid carrier and the spotted probe molecules.

The incubated solid carrier is then washed with an aqueous solvent. The aqueous solvent employed for the washing preferably contains a surface active agent such as sodium dodecyl sulfate or a buffer composition such as a brine-citrate buffer. The washing is preferably conducted in a warm or hot aqueous solvent so as to remove an essentially whole amount of the thickening agent from the surface of the solid carrier and further wash out free probe molecules which have not been fixed onto the carrier.

The DNA detection micro-array of the invention preferably has a great number of spots or dots (generally, from several hundreds to tens of thousands) in which a great number of probe molecules are fixed to the solid carrier by covalent bonding. The UV which is relative to variation of conditions of the different spots preferably is less than 6.5%.

The DNA detection micro-array is then subjected to the blocking process according to the invention which is described hereinbefore.

[Detection of Complementary DNA Fragments]

A target DNA fragment or a sample DNA fragment, which is to be subjected to the analysis concerning the presence of a complementary DNA fragment can be obtained from various origins. In the analysis of gene, the target DNA fragment can be prepared from a cell or tissue of eucaryote. In the analysis of genome, the target DNA fragment can be obtained from tissues other than erythrocyte. In the analysis of mRNA, the target sample is obtained from tissues in which mRNA is expressed. If the DNA micro-array has an oligonucleotide fixed on its solid carrier, the target DNA fragment preferably has a low molecular weight. The target DNA may be multiplied by PCR method.

To the target DNA fragment is attached an RI label or a non-RI label by a known method. The non-RI label is preferably utilized. Examples of the non-RI labels include fluorescence label, biotin label, and chemical luminescence label. The fluorescence label is most preferably employed. Examples of the fluorescence labels include cyanine dyes (e.g., Cy3 and Cy5 belonging to Cy Dye™ series), rhodamine 6G reagent, N-acetoxy-N$^2$-acetyl-aminofluorene (AAF), and AAIF (iodide derivative of AAF). The target or sample DNA fragments labelled with different fluorescence indicators can be simultaneously analyzed, it the fluorescence indicators have fluorescence spectrum of different peaks. Also employable is an electroconductive label.

The hybridization is performed by spotting an aqueous sample solution containing the target DNA fragments onto the DNA micro-array. The spotting is generally done in an amount of less than several $\mu$g, preferably in the range of 1 to 100 nL. The hybridization is carried out by keeping the DNA micro-array having the spotted sample solution thereon at a temperature between room temperature and 70° C., for 6 to 20 hours. After the hybridization is complete, the DNA micro-array is washed with an aqueous buffer solution containing a surface active agent, to remove free (unfixed) sample DNA fragments. The surface active agent preferably is sodium dodecyl sulfate (SDS). The buffer solution may be a citrate buffer solution, a phosphate buffer solution, a borate buffer solution, Tris buffer solution, or Goods buffer solution. The citrate buffer solution is preferably employed.

The hybridization on the DNA micro-array is characteristic in that an extremely small amount of the sample or target DNA fragments can be subjected to the analysis. In order to perform the desired hybridization appropriately, optimum conditions should be determined.

The DNA micro-array having the hybridized DNA fragments on its surface is dried and then subjected to detection of signals of fluorescent label or other label. The fluorescent label is detected by means of a fluorometer. Fluorometers of various types are known. In the fluorometer, the DNA micro-array on which plural spots having the DNA fragments equipped with the fluorescent label are scanned to detect the locations of the target spots.

The present invention is further described by the following examples.

EXAMPLE 1

Blocking of DNA Chip having Covalent Bonding

[1]

(1) Solid Carrier having Vinylsulfonyl Groups

A glass plate (25 mm×75 mm) was dipped in an aqueous solution of 2 wt. % aminopropylethoxysilane (available from Shin-etsu Chemical Industry Co., Ltd.) for 10 minutes and then taken out. The glass plate was subsequently washed with ethanol and dried to 110° C. for 10 minutes, so as to prepare a glass plate having a coat of the aminosilane compound. On the coated glass plate was spotted an aqueous phosphate buffer solution (pH 8.5) containing 5 wt. % of 1,2-bis(vinysulfonylacetamide)-ethane. After one hour, the spotted glass plate was washed with acetonitrile and dried for one hour under reduced pressure, to give a glass plate having on its surface spots of reactive vinylsulfonyl groups.

(2) Fixation of Probe Molecules

Probe molecules (DNA fragments of double strand DNA (454 bp) whose one strand is modified by an amino group at 5'-terminal) is dispersed in a sterilized water to prepare an aqueous dispersion ($1 \times 10^{-6}$ M). The aqueous dispersion was spotted on the glass plate produced in (1) above, and kept overnight at a constant humidity to fix the probe molecules on the glass plate by covalent bonding. Thus produced DNA chip had probe molecules which were aligned in the form of array on its surface.

(3) Blocking Procedure

The DNA chip produced in (2) above was dipped for 30 minutes in one of the following three blocking solutions:

A: Commercially available Denhaldt's solution

B: Aqueous glycine solution [0.1 M glycine+0.1 M NaCl (pH 8.5)]

C: Aqueous blocking solution of the invention [0.1 M glycine, 0.1 M sodium chloride (pH 8.5), 0.2% sodium dodecyl sulfate (SDS), and 2%-dextran sulfate)

The DNA chip was subjected to blocking treatment using one of the above-mentioned solution, heated to 95° C. for 3 minutes, dipped in cold ethanol for 3 minutes, and dried.

(4) Fixation of Target Molecules (Hybridization)

A target DNA (454 bp) which is labelled with a fluorescence label (FluoroLink Cy5, Amasham Pharmacia Biotec Corp.) at the 5'-terminal of one strand was dispersed in 50 µL of an aqueous solution for hybridization (5×SSC solution and 0.5 wt. % SDS). The dispersion was spotted on each of the DNA chips produced in (2) above and then subjected to blocking procedure in (3) above. The DNA chip was covered with a microscopic cover glass and then incubated at 60° C. for 20 hours in a chamber having a constant humidity. Thus incubated DNA chip was washed with a series of washing procedures consisting of a washing with a mixture solution of 0.1 wt. % SDS and 2×SSC at room temperature, a washing with a mixture solution of 0.1 wt. % SDS and 0.2×SSC at 37° C., and a washing with an aqueous 0.2×SSC solution at room temperature.

The DNA chip having been subjected to the washing procedures was centrifuged at 600 rpm for 20 seconds and dried at room temperature.

(5) Fluorometric Measurement of the Surface of DNA Chip

The distribution of the target molecules fixed on the DNA chip by hybridization was studied by fluorometry. Further, the background fluorescence strength was measured on each DNA chip.

(6) Results

Figure 3:
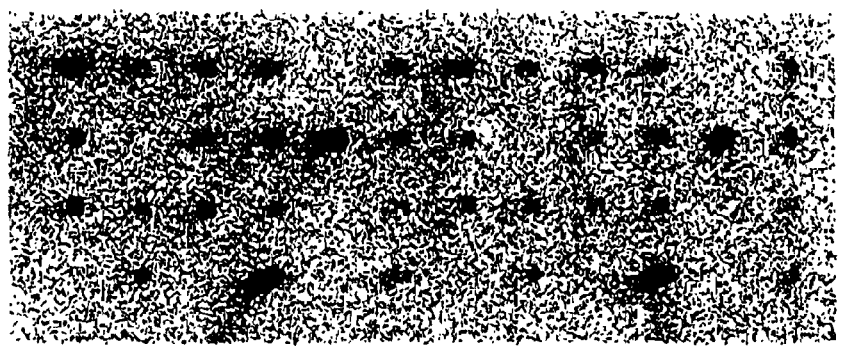
FIG. 3 shows a DNA chip which is blocked and subjected to hybridization in Example 1.
Figure 3:
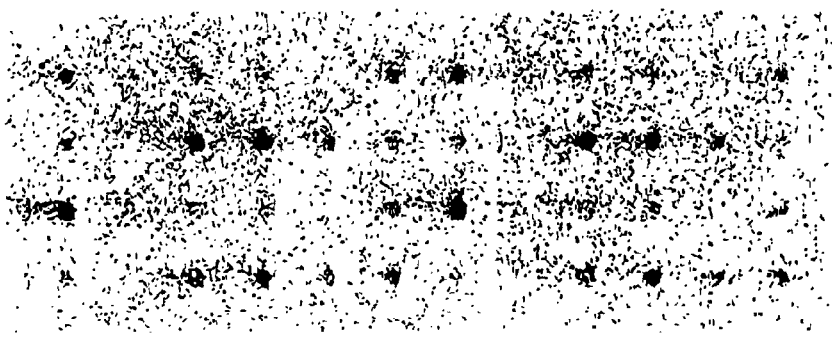
Figure 3:

The image of fluorescence strength observed on each DNA chip on which the target molecules having fluorescence label were fixed is shown in FIG. 3 of the attached drawings.

The background fluorescence strength measured on each DNA chip was given below:

| A (blocked using Denhaldt's solution): | 15,000 |
| B (blocked using aqueous glycine solution): | 12,000 |
| C (blocked using the solution of invention): | 3,500 |

The results shown in FIG. 3 and the background fluorescence strength indicate that the use of the combination of the blocking agents according to the invention greatly reduces the background fluorescence strength and gives spots having a neat shape.

EXAMPLE 2

Blocking of DNA Chip having Covalent Bonding [2]

(1) Production of DNA Chip having Covalently Fixed Probe Molecules

The procedures of (1) and (2) of Example 1 were repeated to produce a DNA chip having probe molecules which were aligned in the form of array on its surface.

(2) Blocking Procedure

The DNA chip produced in (1) above was dipped for 30 minutes in one of the following three blocking solutions:

D: Aqueous glycine/surfactant solution [0.1 M glycine+ 0.1 M NaCl (pH 8.5)+SDS 0.2%]

E: Aqueous glycine solution [0.1 M glycine+0.1 M NaCl (pH 8.5)]

F: Aqueous blocking solution of the invention [0.1 M glycine, 0.1 M sodium chloride (pH 8.5), 0.2% sodium dodecyl sulfate (SDS), and 2% dextran sulfate)

The DNA chip was subjected to blocking treatment using one of the above-mentioned solution, heated to 95° C. for 3 minutes, dipped in cold ethanol for 3 minutes, and dried.

(3) Fixation of Target Molecules (Hybridization)

The hybridization procedure described in (4) of Example 1 were repeated.

(4) Fluorometric Measurement of the Surface of DNA Chip

The distribution of the target molecules fixed on the DNA chip by hybridization was studied by fluorometry. Further, the background fluorescence strength was measured on each DNA chip.

(5) Results

Figure 4:
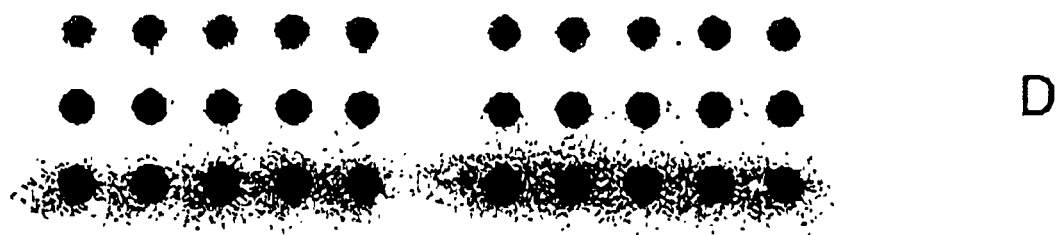
FIG. 4 shows a DNA chip which is blocked and subjected to hybridization in Example 2.
Figure 4:
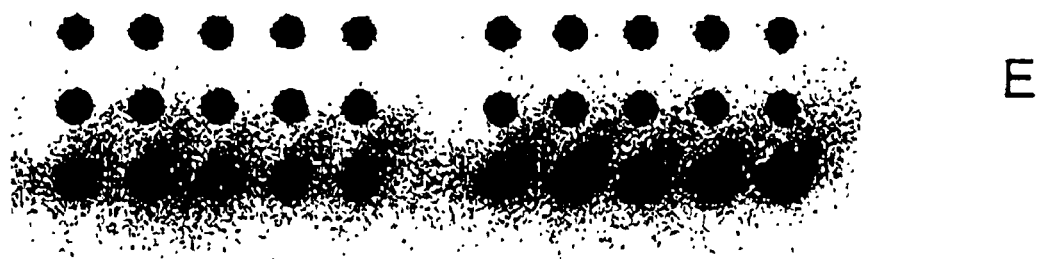
Figure 4:
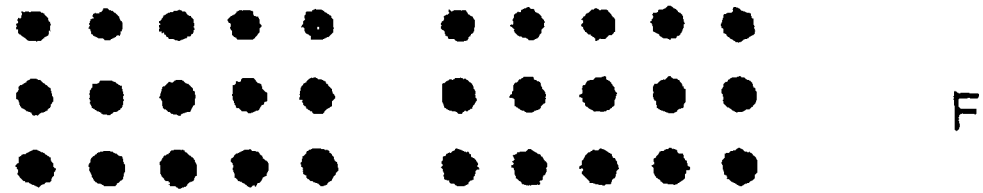

The image of fluorescence strength observed on each DNA chip on which the target molecules having fluorescence label were fixed is shown in FIG. 4 of the attached drawings.

The background fluorescence strength measured on each DNA chip was given below:

| D (blocked using Denhaldt's solution): | 7,500 |
| E (blocked using aqueous glycine solution): | 14,000 |
| F (blocked using the solution of invention): | 3,000 |

The results shown in FIG. 4 and the background fluorescence strength indicate that the use of the combination of the blocking agents according to the invention greatly reduces the background fluorescence strength and gives spots having a neatly figured shape.

EXAMPLE 3

Blocking of DNA Chip having Electrostatic Bonding (1) Production of DNA Chip having Electrostatically Fixed Probe Molecules On a silane-coated glass slide prepared for DNA microarray (GMT-GAPS, available from Corning Corp.) was spotted an aqueous dispersion containing in a sterilized water $1\times10^{-6}$ M of probe molecules (DNA fragments of double strand DNA (454 bp) whose one strand is modified by an amino group at 5'-terminal). The spotted glass slide was heated to 80° C. for one hour and exposed to ultraviolet rays (120 mJ), to produce a DNA chip. Thus produced DNA chip had probe molecules which were fixed by electrostatic bonding and aligned in the form of array on its surface.

(2) Blocking Procedure

The DNA chip produced in (1) above was dipped for 30 minutes in one of the following three blocking solutions:

G: Commercially available Denhaldt's solution

H: Aqueous succinic anhydride solution [which was prepared by dissolving 35 mL of 1-methyl-2-pyrrolidone, 0.01 M boric acid (pH 8.0), and 5 g of succinic anhydride in 315 mL of water]

I: Aqueous blocking solution of the invention [0.1 M glycine, 0.1 M sodium chloride (pH 8.5), 0.2% sodium dodecyl sulfate (SDS), and 2% dextran sulfate)

The DNA chip was subjected to blocking treatment using one of the above-mentioned solution, heated to 95° C. for 3 minutes, dipped in cold ethanol for 3 minutes, and dried.

(3) Fixation of Target Molecules (Hybridization)

The hybridization procedure described in (4) of Example 1 were repeated.

(4) Fluorometric Measurement of the Surface of DNA Chip

The distribution of the target molecules fixed on the DNA chip by hybridization was studied by fluorometry. Further, the background fluorescence strength was measured on each DNA chip.

(5) Results

Figure 5:
FIG. 5 shows a DNA chip which is blocked and subjected to hybridization in Example 3.
Figure 5:
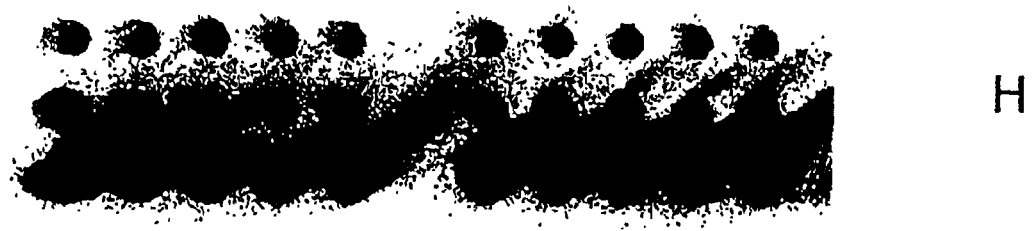
Figure 5:
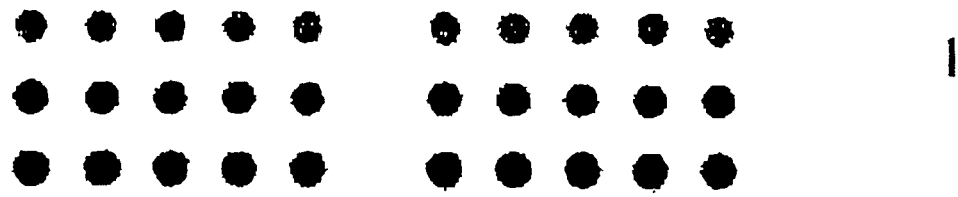

The image of fluorescence strength observed on each DNA chip on which the target molecules having fluorescence label were fixed is shown in FIG. 5 of the attached drawings.

The background fluorescence strength measured on each DNA chip was given below:

| | |
|---|---|
| G (blocked using Denhaldt's solution): | 8,000 |
| H (blocked using aqueous succinic anhydride solution): | 4,500 |
| I (blocked using the solution of invention): | 2,500 |

The results shown in FIG. 5 and the background fluorescence strength indicate that the use of the combination of the blocking agents according to the invention greatly reduces the background fluorescence strength and gives spots having a neat shape.

What is claimed is:

1. A process for treating a device for detection of biochemically active molecules which comprises the steps of:
bringing in the presence of an aqueous medium a detection device having probe molecules, ionic reactive groups, and non-ionic reactive groups on a surface thereof, into contact with compounds which react with the nonionic reactive groups to produce covalent bondings and compounds other than the above mentioned compounds which form electrostatic bondings in conjunction with the ionic reactive groups, simultaneously or separately; and
washing the surface of the detection device with an aqueous solvent or a water-miscible solvent.

2. The process of claim 1, wherein the compounds which react with the non-ionic reactive groups to produce covalent bondings and the compounds which form electrostatic bondings in conjunction with the ionic reactive groups are present in one aqueous solution.

3. The process of claim 1, wherein the aqueous medium contains a surface active agent.

4. The process of claim 1, wherein the ionic reactive groups are amino groups or mercapto groups.

5. The process of claim 1, wherein the ionic reactive groups are amino groups and the compounds which form electrostatic bondings in conjunction with the ionic reactive groups are dextran sulfates.

6. The process of claim 1, wherein the non-ionic reactive groups are ethylenic unsaturated groups.

7. The process of claim 6, wherein the ethylenic unsaturated groups are vinylsulfonyl groups or their precursors having the formula:

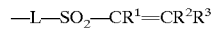

wherein each of $R^1$, $R^2$ and $R^3$ independently is a hydrogen atom, an alkyl group having 1 to 6 carbon atoms, an aryl group having 6 to 20 carbon atoms, or an aralkyl group having 7 to 26 carbon atoms in which its alkyl group has 1 to 6 carbon atoms, and L is a linking group.

8. The process of claim 1, wherein the non-ionic reactive groups are ethylenic unsaturated groups and the compounds which react with the non-ionic reactive groups to produce covalent bondings are amino group-containing compounds.

9. The process of claim 8, wherein the amino group-containing compounds are glycines.

10. The process of claim 1, wherein the probe molecules are nucleotide derivatives selected from the group consisting of oligonucleotides, polynucleotides, and peptide nucleotic acids.

11. The process of claim 1, wherein the probe molecules, ionic reactive groups, and non-ionic reactive groups are fixed on the detection device by covalent bonding.

12. A process for treating a device for detection of biochemically active molecules which comprises the steps of:
bringing in the presence of an aqueous medium a detection device having probe molecules and amino groups on a surface thereof, into contact with compounds selected from the group consisting of dextran sulfate, mucopolysaccharide having sulfonyl group, taurine having sulfonyl group, polypeptide having carboxyl group, and polysaccharide having carboxyl group which form electrostatic bondings in conjunction with the amino groups; and
washing the surface of the detection device with aqueous solvent or a water-miscible solvent.

13. The process of claim 12, wherein the aqueous medium contains a surface active agent.

14. The process of claim 12, wherein the ionic reactive groups are amino groups or mercapto groups.

15. The process of claim 12, wherein the probe molecules are nucleotide derivatives selected from the group consisting of oligonucleotides, polynucleotides, and peptide nucleotic acids.

16. The process of claim 12, wherein the probe molecules are fixed on the detection device by electrostatic bonding and ionic reactive groups are fixed on the detection device by covalent bonding.

* * * * *